United States Patent
Mirkin et al.

(10) Patent No.: US 9,969,759 B2
(45) Date of Patent: May 15, 2018

(54) DUPLEX-SELECTIVE ORGANOMETALLIC DNA INTERCALATORS

(71) Applicant: NORTHWESTERN UNIVERSITY, Evanston, IL (US)

(72) Inventors: Chad A. Mirkin, Wilmette, IL (US); Chad M. Shade, Chicago, IL (US); Robert D. Kennedy, Midland, MI (US); Jessica Lynn Rouge, Evanston, IL (US); Soyoung E. Seo, Evanston, IL (US); Mary X. Wang, Evanston, IL (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 0 days. days.

(21) Appl. No.: 15/312,221

(22) PCT Filed: May 22, 2015

(86) PCT No.: PCT/US2015/032130
§ 371 (c)(1),
(2) Date: Nov. 18, 2016

(87) PCT Pub. No.: WO2015/179736
PCT Pub. Date: Nov. 26, 2015

(65) Prior Publication Data
US 2017/0082614 A1 Mar. 23, 2017

Related U.S. Application Data

(60) Provisional application No. 62/138,128, filed on Mar. 25, 2015, provisional application No. 62/001,982, filed on May 22, 2014.

(51) Int. Cl.
C07F 15/00 (2006.01)
C12Q 1/68 (2018.01)
C07H 23/00 (2006.01)
G01N 27/447 (2006.01)
(Continued)

(52) U.S. Cl.
CPC ......... C07F 15/0053 (2013.01); C07H 23/00 (2013.01); C12Q 1/6816 (2013.01); G01N 27/44726 (2013.01); G01N 27/44747 (2013.01); G01N 33/5308 (2013.01); G01N 33/582 (2013.01); G01N 33/587 (2013.01)

(58) Field of Classification Search
CPC .......................... C07F 15/0026; C12Q 1/6816
USPC ........................................... 514/185; 435/6.1
See application file for complete search history.

(56) References Cited

U.S. PATENT DOCUMENTS

| | | |
|---|---|---|
| 3,687,808 A | 8/1972 | Merigan et al. |
| 5,432,272 A | 7/1995 | Benner |
| 2005/0148772 A1 | 7/2005 | Barton et al. |

(Continued)

OTHER PUBLICATIONS

Coates et al., Probing the Interaction of [Ru(phen)$_2$(dppz)]$^{2+}$ with Single-Stranded DNA—What Degree of Protection is Required for Operation of the "Light-Switch Effect"?, J. Phys. Chem. B, 105(3):730-5 (2001).

(Continued)

Primary Examiner — Jezia Riley
(74) Attorney, Agent, or Firm — Marshall, Gerstein & Borun LLP

(57) ABSTRACT

Disclosed herein are organometallic complexes and methods of using the same in detecting double stranded DNA or RNA, selectively over single stranded DNA or RNA.

18 Claims, 4 Drawing Sheets

(51) Int. Cl.
*G01N 33/53* (2006.01)
*G01N 33/58* (2006.01)

(56) References Cited

U.S. PATENT DOCUMENTS

2007/0224612 A1 9/2007 Barton et al.
2009/0131640 A1 5/2009 Berkelman
2009/0221095 A1 9/2009 Mirkin et al.
2013/0331367 A1 12/2013 McFarland

OTHER PUBLICATIONS

Cook, Medicinal chemistry of antisense oligonucleotides—future opportunities. Anticancer Drug Des., 6(6):585-607 (1991).
Dickeson et al., Derivatives of 1,10-Phenanthroline-5,6-quinone, Aust. J. Chem., 23(5):1023-7 (1970).
Englisch et al., Chemically modified oligonucleotides as probes and inhibitors, Ang. Chem. Int. Ed., 30:613-29 (1991).
Evans et al., Dichlorotetrakis(dimethyl sulphoxide)ruthenium(II) and its use as a source material for some new ruthenium(II) complexes, J. Chem. Soc., Dalton Trans., 1973(2):204-9 (1973).
Freier et al., The ups and downs of nucleic acid duplex stability: structure-stability studies on chemically-modified DNA:RNA duplexes, Nucleic Acids Res., 25:4429-43 (1997).
Friedman et al., A molecular light switch for DNA: Ru(bpy)2(dppz)2+, J. Am. Chem. Soc., 112(12):4960-2 (1990).
Hartshorn et al., Novel dipyridophenazine complexes of ruthenium(II): exploring luminescent reporters of DNA, J. Am. Chem. Soc., 114(15):5919-25 (1992).
Hudali et al., Some transition-metal chelates with 8-amino-, 8-(diphenylphosphino)-, and 8-(diphenylarsino)quinoline bidentate ligands, Inorg. Chem., 18(5):1391-4 (1979).
International Search Report and Written Opinion, International Application No. PCT/US15/032130, dated Oct. 13, 2015.
Jenkins et al., A sequence-specific molecular light switch: tethering of an oligonucleotide to a dipyridophenazine complex of ruthenium(II), 114(22):8736-8 (1992).
Kroschwitz (ed.), The Concise Encyclopedia of Polymer Science and Engineering, pp. 858-859, New York: John Wiley & Sons (1990).
Liu et al., Interaction of $[Ru(dmp)_2(dppz)]^{2+}$ and $[Ru(dmb)_2(dppz)]^{2+}$ with DNA—Effects of the Ancillary Ligands on the DNA-Binding Behaviors, Inorg. Chem., 40(19):5045-50 (2001).
Niyazi et al., Crystal structures of $\Lambda$-$[Ru(phen)_2dppz]^{2+}$ with oligonucleotides containing TA/TA and AT/AT steps show two intercalation modes, Nat. Chem., 4(8):621-8 (2012).
Prigodich et al., Multiplexed nanoflares: mRNA detection in live cells, Anal. Chem., 84(4):2062-6 (2012).
Sanghvi, Heterocyclic base modifications in nucleic acids and their applications in antisense oligonucleotides, Chapter 15 in Crooke et al. (eds.), Antisense Research and Applications, CRC Press (1993).
Seferos et al., Nano-flares: probes for transfection and mRNA detection in living cells, J. Am. Chem. Soc., 129(50):15477-9 (2007).
Song et al., Crystal structure of $\Delta$-$[Ru(bpy)_2dppz]^{2+}$ bound to mismatched DNA reveals side-by-side metalloinsertion and intercalation, Nat. Chem., 4(8):615-20 (2012).
Sullivan et al., Mixed phosphine 2,2'-bipyridine complexes of ruthenium, Inorg. Chem., 17(12):3334-41 (1978).
van der Drift et al., Ruthenium-Catalyzed Isomerization of Allylic Alcohols: Oxidation State Determines Resistance Against Diene Inhibition, Eur. J. Inorg. Chem., 2002(8):2147-55 (2002).

SEQUENCE LISTING

```
<160> NUMBER OF SEQ ID NOS: 16

<210> SEQ ID NO 1
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 1
ttgctgagta tgagtgaa                                                18

<210> SEQ ID NO 2
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 2
ttcactcata ctcagcaa                                                18

<210> SEQ ID NO 3
<211> LENGTH: 6
<212> TYPE: DNA
<213> ORGANISM: Artificial Sequence
<220> FEATURE:
<223> OTHER INFORMATION: Synthetic polynucleotide

<400> SEQUENCE: 3 aggtga                                                              6

<210> SEQ ID NO 4
<211> LENGTH: 6
<212> TYPE: DNA
<213> ORGANISM: Artificial Sequence
<220> FEATURE:
<223> OTHER INFORMATION: Synthetic polynucleotide

<400> SEQUENCE: 4 tcacct                                                              6

<210> SEQ ID NO 5
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 5
aggtgagtat gagtcgtt                                                18

<210> SEQ ID NO 6
```

```
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 6
aacgactcat actcacct                                                    18

<210> SEQ ID NO 7
<211> LENGTH: 36
<212> TYPE: DNA
<213> ORGANISM: Artificial Sequence
<220> FEATURE:
<223> OTHER INFORMATION: Synthetic polynucleotide

<400> SEQUENCE: 7
agtcacgacg agtcattcct tagtcacgac gagtca                                36

<210> SEQ ID NO 8
<211> LENGTH: 36
<212> TYPE: DNA
<213> ORGANISM: Artificial Sequence
<220> FEATURE:
<223> OTHER INFORMATION: Synthetic polynucleotide

<400> SEQUENCE: 8
tgactcgtcg tgactaagga atgactcgtc gtgact                                36

<210> SEQ ID NO 9
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 9
atttcaatgt gattagtt                                                    18

<210> SEQ ID NO 10
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 10
aactaatcac attgaaat                                                    18

<210> SEQ ID NO 11
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 11
aggtgagtat gagtcgtt                                                    18

<210> SEQ ID NO 12
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 12
```

```
aacgactcat actcacct                                                 18

<210> SEQ ID NO 13
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 13
ctttcagtcc cacccccc                                                 18

<210> SEQ ID NO 14
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 14 gggggggtggg actgaaag                                                18

<210> SEQ ID NO 15
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 15
ccctccgtcc cccccccc                                                 18

<210> SEQ ID NO 16
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 16
gggggggggg acggaggg                                                 18
```

DUPLEX-SELECTIVE ORGANOMETALLIC DNA INTERCALATORS

CROSS REFERENCE TO RELATED APPLICATIONS

This application claims the benefit of U.S. Provisional Application No. 62/001,982, filed May 22, 2014, and U.S. Provisional Application No. 62/138,128, filed Mar. 25, 2015, the disclosure of each is incorporated by reference in its entirety herein.

STATEMENT OF GOVERNMENT SUPPORT

This invention was made with government support under grant number U54 CA151880 awarded by the National Institutes of Health; grant number W911NF-11-1-0229 awarded by the Army Research Office; grant numbers CHE1149314 and DMR1121262 awarded by the National Science Foundation; grant numbers FA9550-12-1-0141, FA9550-11-1-0275 and FA9550-12-1-0280 awarded by the Air Force Office of Scientific Research; and grant number HR0011-13-2-0018 awarded by the Defense Advanced Research Projects Agency (DARPA). The government has certain rights in the invention.

BACKGROUND

For many decades, gel electrophoresis has been the preferred method for the separation and characterization of nucleic acids. The imaging of nucleic acids within these gels is currently possible via small molecule staining agents, which provide a measureable colocalized response. Nucleic acid stains typically possess planar, conjugated π systems with excited-state photophysical properties, which allows them to be visualized using fluorescence gel plate readers. The sensitivity of these methods relies on structures that luminesce in a nucleic acid environment but are quenched by the surrounding hydrogel matrix, thus reducing the overall background signal. Although it is possible to perform gel electrophoresis under denaturing conditions in order to remove the presence of base-pairing and other intramolecular interactions, running the gel under conditions that support hybridization to distinguish single-stranded DNA (ssDNA) from its duplex state could provide additional useful information regarding the structural state of the nucleic acids. Such information would be particularly helpful in applications which rely on differentiating the amount of double stranded DNA (dsDNA) from ssDNA, such as the DNA amplification step involved in polymerase chain reactions (PCR). To date, identifying molecules that exhibit specific interactions for dsDNA rather than ssDNA, both in solution and within gel electrophoresis assays, remains a challenge.

SUMMARY

Disclosed herein are organometallic complexes having a structure M(Het)(Het)(L), wherein M is Ru or Os; each Het is independently bipyridyl, phenanthrolinyl, bipyridyl substituted with one or more of $C_{1-6}$alkyl and $C_{1-10}$alkylene-$CO_2R$, or phenanthrolinyl substituted with one or more of $C_{1-6}$alkyl and $C_{1-10}$alkylene-$CO_2R$, and R is null, H, $C_{1-6}$alkyl, or an oligonucleotide moiety; and L is a structure:

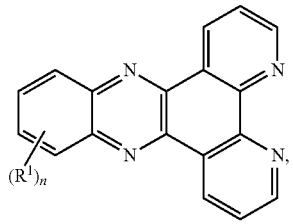

wherein n is 0-3, and each $R^1$ is independently selected from $C_{1-6}$alkyl, CN, $NO_2$, $OC_{1-6}$alkyl, $CO_2H$, and $CO_2C_{1-6}$alkyl, with the proviso that when n is 0 at least one Het is substituted with $C_{1-10}$alkyl-$CO_2R$. Further disclosed are salts of the organometallic complex, e.g., a chloride, hexaflurophosphate, or sodium salt.

Further provided herein are conjugates of the organometallic complexes disclosed herein and an oligonucleotide. In some cases, at least one R of the complex comprises an oligonucleotide moiety, and the oligonucleotide of the conjugate has a sequence that is sufficiently complementary to the sequence of the oligonucleotide moiety to hybridize to the oligonucleotide moiety of the complex. Also provided are nanoparticles comprising a plurality of cross-linked oligonucleotides and at least one conjugate or complex as disclosed herein.

Further provided are methods of detecting a target molecule in a sample using the complexes disclosed herein by contacting the sample with a complex under conditions that allow association of the target molecule with the complex, wherein upon association of the target molecule and the complex, the complex undergoes a detectable change, said change indicative of the presence of the target molecule. The detectable change can be fluorescence, color change, absorbance, or the like. The detectable change can be proportional to the concentration of the target molecule in the sample. The target molecule can be double stranded DNA or double stranded RNA. The complex can be selective for dsDNA compared to ssDNA. The complex can be selective for dsRNA compared to ssRNA. The enhancement factor (E.F.) of the complex can be at least 10, at least 30, or at least 50 for dsDNA (or dsRNA) compared to ssDNA (or ssRNA). These methods can be used in gel electrophoresis and/or in intracellular detection of the target molecule.

DETAILED DESCRIPTION

Figure 1:
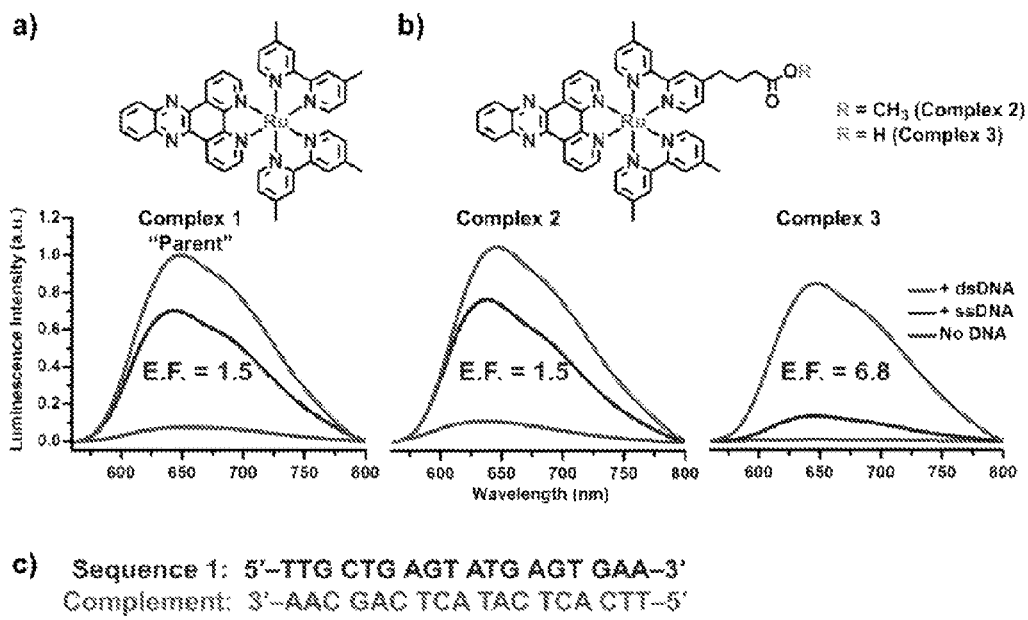
FIG. 1 shows luminescence intensities of complexes 1, 2, and 3 at 3 µM upon interaction with 10 µM of ssDNA and dsDNA in buffer (PBS, 10 mM, pH 7.5) at 25° C. a) Emission profiles of complex 1 in the presence of ssDNA vs dsDNA and for b) complexes 2 and 3, respectively. The temperature of the samples was maintained at 25° C., and the counter anion for all complexes was Cl$^-$. c) The 18 base DNA sequences used in fluorescence assays.

There are commercially-available options for detecting DNA hybridization events using luminescent reports and observing target binding as an increase in fluorescence signal. Nano-flares represent one such class of luminescent reporters and the sensing aspect is manifested in the relative proximity of molecular fluorophore and plasmonic nanoparticle before and after targeted hybridization has occurred.[1,2] However, if one were to design a sensing motif that no longer relies upon the quenching properties afforded by plasmon-exciton interactions, attention must be shifted toward incorporating luminescent components which are themselves quenched in the absence of DNA duplexes. Several design features are common among the myriad forms of small molecules which interact and provide an enhanced luminescence response in the presence of DNA duplexes. Most carry a positive charge in the local environment adjacent to the intercalation site in addition to planarity in the form of extended conjugated ligand structures which also imparts luminescent properties. Several reports in the literature describe DNA duplex intercalators which luminesce only while protected from the quenching environment. One well-known examples of these is the dipyridophenazine ("dppz") subclass of ruthenium-based intercalator complexes,[3,4] and the intercalation of DNA duplexes by these complexes has been recently characterized through crystal structure.[5,6] While the reported four-orders-of-magnitude enhancement of the "light-switch" complex is impressive,[3] it is important to note that this fluorescence enhancement is between the complex dissolved in protic solvents and in aqueous solutions containing annealed DNA duplexes, and the realization of these molecules as true luminescent reporters for duplex DNA is hampered by their non-specific and perhaps even less well-known interactions with single-stranded oligonucleotides.[7] There is at least one demonstration of a duplex-specific dipyridophenazine complex,[8] a structurally-similar analog which presents two pendant acid chains from the ligands not directly involved with DNA duplex intercalation. One of these acid groups in this example has been utilized to covalently append the complex to an amine-labeled oligonucleotide sequence through the ancillary ligand and it was in this context that the reader may judge the selectivity of the complex for duplexed DNA over single-stranded oligonucleotides. Therefore, the selectivity of the free molecular system for duplex DNA as compared to its non-acid-bearing parent counterpart is unknown.

It is with these design aspects in mind that the number and nature of functional groups presented by the so-called ancillary ligands was investigated to thus define the local environment around dipyridophenazine ruthenium complexes, with the ultimate goal of maintaining a luminescent response in the presence of DNA hybridization while reducing the background luminescence signal in the presence of unhybridized single-stranded oligonucleotides. This study was enabled both by ligand design, identifying an ancillary ligand which allows for the installation of one or two pendant functional groups while maintaining the overall electronic structure of the parent complex, and by the modular ruthenium complex synthesis, the facile incorporation of the intercalating ligand and various combinations of functionalized and non-functionalized ancillary ligands. The ancillary ligand of choice, 4,4'-dimethyl-2,2'-bipyridine ("dmb"), was utilized herein both as a non-functionalized ancillary ligand and also as a functionalized component through stoichiometric lithiation reactions in the presence of brominated acetals and subsequent hydrolysis, and over the course of oxidation and esterification, four functionalized polypyridyl ligands were produced, bearing either one or two functional groups (dmb'-$CO_2$R and dmb'-($CO_2$R)$_2$, where R=H, $CH_3$). The intercalating ligand was designed to be a maintained structural component, incorporated into a mono-ligated starting material by refluxing a divalent ruthenium salt precursor (Ru(DMSO)$_4$Cl$_2$)[9,10] in the presence of one equivalent of dipyridophenazine ligand (Ru(dppz)(DMSO)$_2$Cl$_2$). Occupying the remaining two coordination sites with all possible combinations of the functionalized and non-functionalized diimine ligands resulted in a parent complex and three families of functionalized complexes, each possessing, one, two, or three pendant functional groups (ten complexes in total, including the parent complex). The ability to detect duplexed over single-stranded oligonucleotides follows a general trend within each family and across the entire series of complexes synthesized, namely, greater numbers of negatively charged functional groups lead to overall better signal enhancements compared to their ester counterparts by reducing the signal produced as a result of single-stranded interactions. A trade-off in enhancement was identified as the complexes become too sterically hindered and electrostatically repelled by the duplex to maintain a sufficient number of emitted photons.

A rational design approach for small molecules is presented herein that provide enhanced luminescence signals in the presence of duplexed rather than single-stranded DNA. These molecules were realized by synthetically addressing the local environment presented by a ruthenium-based DNA intercalator through modification of the ancillary ligands. First, a ligand system was selected so that either one or two functional groups, in this case esters or acids, could be appended to each ancillary ligand via a robust alkyl spacer region. Next, ruthenium complexes were synthesized by assembling various combinations of functionalized and non-functionalized ligands in a modular synthetic approach. Finally, the luminescence response of these complexes was characterized in the presence of single-stranded and fully-duplexed oligonucleotides. The enhanced selectivity for duplexed-oligonucleotides follows a general trend, suggesting the increased polarity of the acid groups outweighs the benefits of decreased steric accessibility afforded by the esters.

Figure 4:
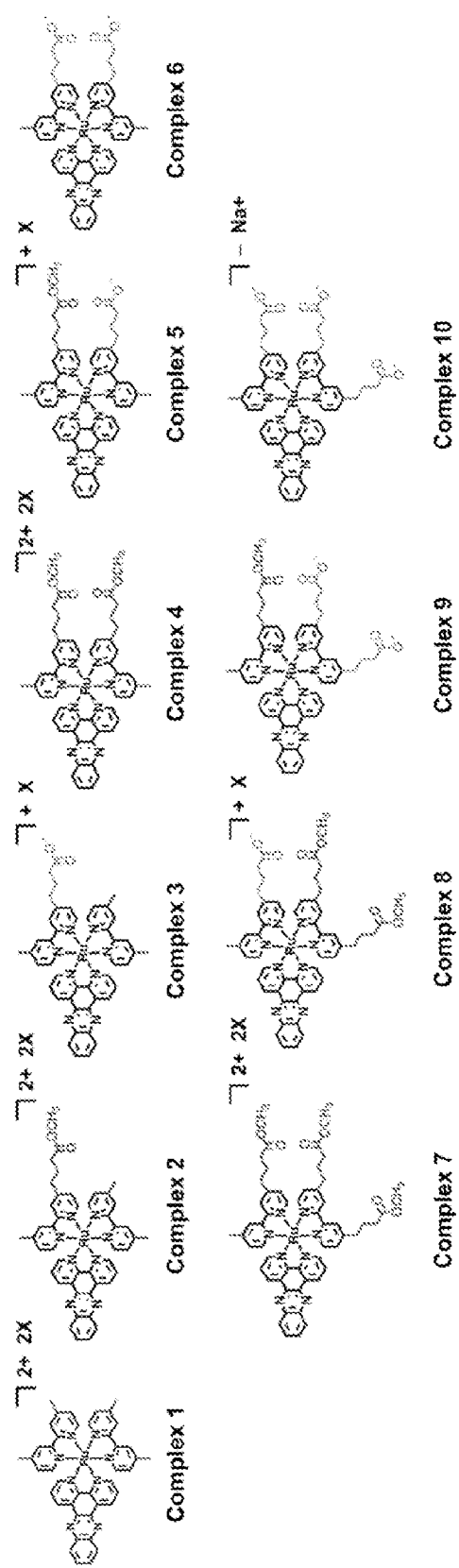
FIG. 4 is a schematic representation of intercalator complexes disclosed herein (Complexes 1-10). X=$PF_6^-$ as synthesized or Cl$^-$ after salt exchange.

The oligonucleotide sequences chosen to investigate oligonucleotide selectivity are presented in Table 1. The main sequence is used extensively for the programmed assembly of DNA-functionalized nanoparticles into crystallographically-ordered aggregates. It is an appropriate sequence to use in these investigations because it does not present thermodynamically-favorable Watson-Crick base pairings at the temperature and ionic strength specified in the current study, and the parameters necessary to hybridize to its complementary strand are known. The luminescence of the parent complex, [Ru(dmb)$_2$(dppz)]$^{2+}$, was measured in phosphate-buffered saline and in solutions containing either the unhybridized sequence or the sequence annealed to its complement (Complex 1, FIG. 1a, FIG. 4).

As is the case with similarly charged complexes reported in literature,[7] Complex 1 is mostly quenched in buffer solution, but luminesces quite strongly in the presence of either single-strands or DNA duplexes. To quantify the difference between luminescence signals produced in solutions containing single-stranded versus duplexed oligonucleotides, the following mathematical relationship was defined to evaluate selectivity, which was termed enhancement factor (E.F.)

$$E.F. = \frac{I_{(dsDNA-Buffer)}}{I_{(ssDNA-Buffer)}}$$

where I refers to integrated luminescence intensity of the ruthenium(II) complex. In this manner, complex 1 was observed to emit approximately 1.5 times more photons in the presence of dsDNA than it does in the presence of ssDNA (FIG. 1a).

Although the true physical nature of this interaction between complex and single-stranded oligonucleotides is yet unknown to the field,[7] it is hypothesized that it is at least initially electrostatic in nature, with the divalent complex serving as a countercation, and that the oligonucleotide is free to coil around the complex in such a way that the DNA bases protect the excited state of the complex from non-radiative routes of energy transfer. If true, designing ligand systems that prevent the initial attraction and subsequent coiling of single-stranded DNA should reduce the un-hybridized oligonucleotide luminescence response. The first modification introduced to the parent complex is a single methyl ester substituted at one of the methyl positions of dimethylbipyridine via a propyl spacer, reserving the final ligand coordination sites for an unmodified dimethylbipyridine, [Ru(dppz)(dmb'-CO$_2$CH$_3$)(dmb)]$^{2+}$. The methyl ester arm could have been considered to present at least some steric hindrance compared to the parent complex and that interactions between single-stranded oligonucleotides would be reduced, however, virtually no improvements in luminescent selectivity for this particular species was observed (Complex 2, FIG. 1b). It is important to also note that the maximum integrated luminescence intensity observed in the presence of duplexed DNA for these two complexes is well within 5%, suggesting that the modification made to Complex 2 does not compromise the degree to which intercalation can occur, Saponification of the ester arm, resulting in [Ru(dppz)(dmb'-CO$_2^-$)(dmb)]$^{1+}$ (Complex 3, FIG. 1b), produces more profound effects on both the relative intensity of the intercalated state and on the luminescence selectivity of duplexed versus single-stranded oligonucleotides. The pKa of the acid group is about 4.5, and modifying the net charge and specifically the charge density in the local environment of Complex 3 could limit its overall effectiveness as a countercation but, more importantly, not in such a way that significantly attenuates intercalation into DNA duplexes. Compared to either the parent system or the ester-functionalized complex, the relative intensity of the intercalated state decreases by approximately 10% for the acid-functionalized Complex 3 yet the luminescence selectivity over single-stranded oligonucleotides sees much more significant gains, increasing from an E.F. of 1.5 to an E.F. of 6.8 (FIG. 1b) indicating that the local charge density reduced the interaction between the complex and ssDNA. However, modification of complex charge does not impede the intercalation of the complex into the DNA duplex.

The introduction of a second pendant ester chain, this time by replacing both dimethylbipyridines with singly-functionalized ligands, results in [Ru(dppz)(dmb'-CO$_2$CH$_3$)$_2$]$^{2+}$ (Complex 4), which is similar in charge to both Complex 1 and Complex 2. To determine the effect of steric interactions, complex 2 was compared to complex 4 ([Ru(dppz)(dmb'-CO$_2$CH$_3$)$_2$]Cl$_2$), which possess one and two pendant ester groups, respectively. Since complex 4 has a 3-fold higher E.F. than complex 2, it was hypothesized that increasing the steric bulkiness of the intercalator ancillary ligand promotes dsDNA selectivity. To further investigate the role of electrostatic repulsion, one of the ester-functionalized ligands was replaced with a carboxylic acid-functionalized ligand. This results in an intercalator, [Ru(dppz)(dmb'-CO$_2$CH$_3$)(dmb'-CO$_2^-$)]Cl (complex 5), that displays a significantly higher E.F. than both complex 4, which possesses the same number of pendant groups but a different overall charge, and complex 3, which has a different number of pendant groups but has the same charge. Based on the observations that two esters lead to greater enhancement than a single ester (complex 4>complex 2) and that the combination of an ester group and a carboxylate results in greater enhancement than a single carboxylate (complex 5>complex 3), it was hypothesized that increased electrostatic repulsion might result in the most dramatic enhancement in selectivity. Thus, complex 6 was prepared [Ru(dppz)(dmb'-CO$_2^-$)$_2$], which has two pendant chains, both of which terminate in carboxylates. This net neutral complex exhibited a remarkable E.F. of 58, which is two-fold higher than the second most selective compound (complex 5). From this series of complexes, it is apparent that increasing the electrostatic repulsion between the ancillary ligands and the negatively charged backbone of the DNA helix most significantly increases duplex specific luminescence, while steric hindrance plays a noticeable but smaller role.

Figure 3:
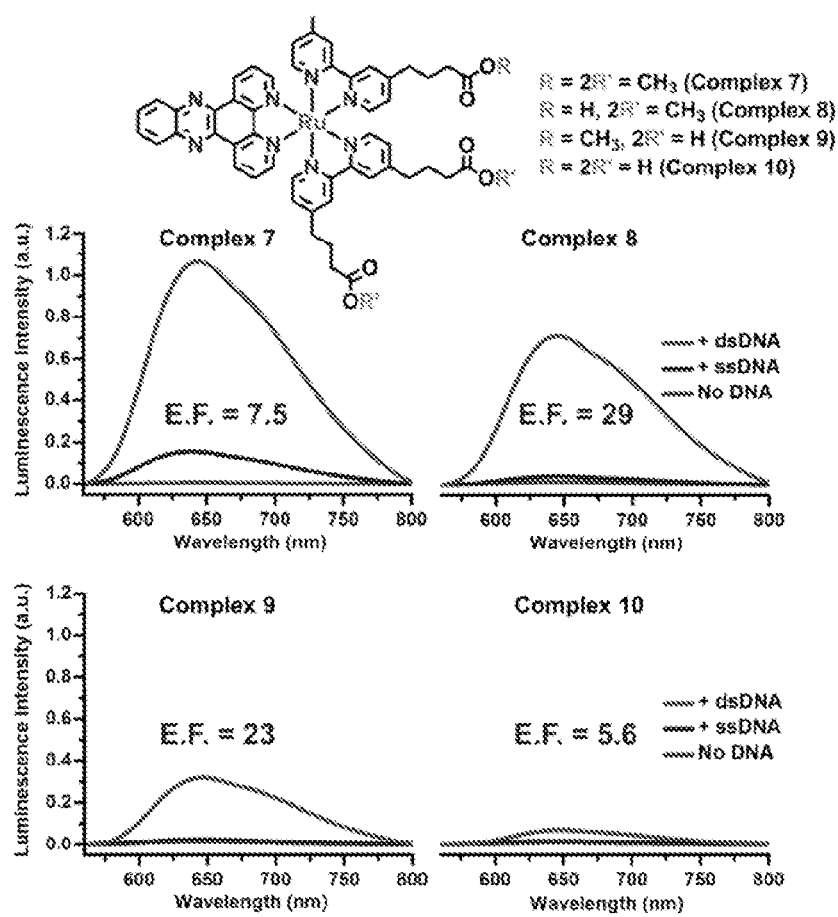
FIG. 3 shows fluorescence intensities of complexes 7, 8, 9, and 10 at 3 µM upon interaction with 10 µM dsDNA and ssDNA in buffer (PBS, 10 mM, pH 7.5) at 25° C. The counter anion for all complexes was Cl$^-$.

Next, the replacement of one of the two singly-functionalized ancillary ligands for a ligand that is twice functionalized was investigated. A new class of ligand was synthesized in a manner analogous to the preparation of bpy'-CO$_2$R by adjusting the stoichiometric parameters of the initial lithiation reaction, preserving both the length and relative location of the new functionalized arm. The new bpy"-(CO$_2$R)$_2$ ligands (where 'R' is once again either H or CH$_3$) preserve the electronic structure of the resulting complexes, that they would therefore serve as good models to study alongside either of the previously discussed complex systems. All of the possible 1:1 combinations of singly and doubly-functionalized ancillary ligands were assembled in addition to the site already dedicated to the intercalating moiety, resulting in four tris-heteroligated complexes that each possess three functional groups (Complexes 7-10). In doing so, not only was a similar trend in selectivity observed that was consistent with the structure-activity relationships demonstrated as being important (FIG. 3), but the practical limitations of this approach were identified, which is also internally-consistent with the working hypothesis of oligonucleotide-complex interactions. Unlike complexes containing either one or two functional groups (Complexes 2-3 and 4-6, respectively), having three pendant arms does seem to be the ultimate limit in terms of the complex being able to maintain sufficiently high relative luminescence intensities in the presence of duplexes which no longer outpace selectivity. This last point does not seem to be relevant to the new, three ester-containing Complex 7, especially when studied alongside the other ester-functionalized complexes in the series. The E.F. follows the trend: complex 7>complex 4>complex 2, making it apparent that greater steric bulk leads to enhancement of duplex selectivity. Still, steric interactions of the ester-functionalized chains are less effective at increasing duplex selectivity than the introduction of acid-functionalized chains, since complex 7 is far less enhancing than either complex 5 or complex 6. This is further demonstrated when one of the three pendant ligands becomes an acid group, as in [Ru(dppz)(dmb'-$CO_2CH_3$)$_2$(dmb'-$CO_2^-$)]Cl (complex 8), which has an almost 3-fold higher E.F. than complex 7.

The role of ester versus acid is much better visualized among the family of complexes which each contain three functional groups. In the remaining two complexes of the tris-heteroligated family, complexes 9 and 10, we have identified the limitations of this approach for increasing duplex specificity. Further modification of the ligands appears to compromise the interaction of the complex with dsDNA. For example, [Ru(dppz)(dmb'-$CO_2CH_3$)(dmb'-$CO_2^-$)$_2$] (complex 9), which possesses two pendant acid groups and one pendant ester group, has a lower E.F. than the sterically similar complex 8. The extra pendant arm on complex 9 reduces the E.F. to far below that of the other net neutral molecule, complex 6. The molecule with an overall negative charge, Na[Ru(dppz)(dmb'-$CO_2^-$)$_3$] (complex 10), does not exhibit significant luminescence in the presence of dsDNA. Presumably, this stems from an inability of the complex to bind to or intercalate into dsDNA due to the barrier presented by the steric hindrance and unfavorable electrostatic interaction introduced through the numerous negatively charged pendant groups.

Figure 2:
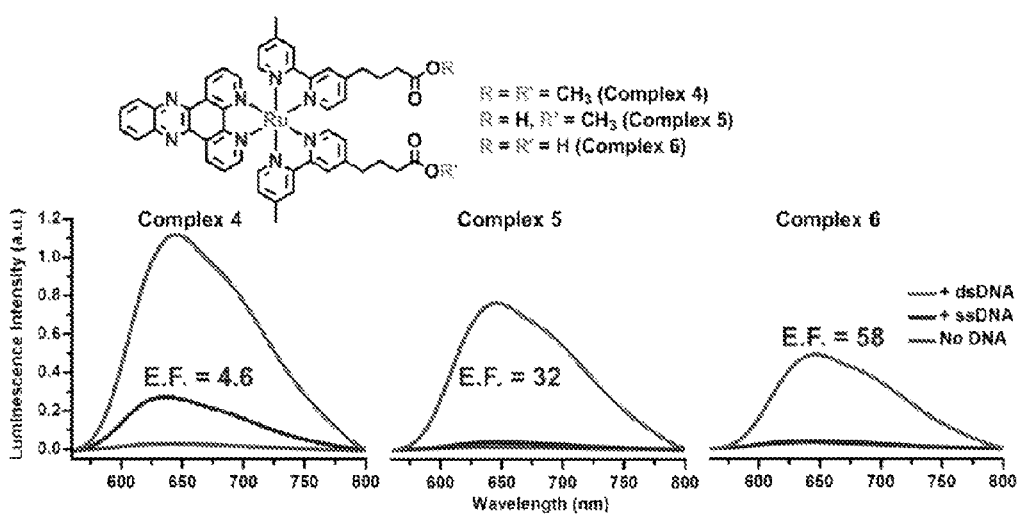
FIG. 2 shows fluorescence intensities of complexes 4, 5, and 6 at 3 µM upon interaction with 10 µM of dsDNA and ssDNA in buffer (PBS, 10 mM, pH 7.5) at 25° C. The counter anion for all complexes was Cl$^-$.

Although this trend of increased enhancement factor continues for Complex 8 as compared to Complex 7, the decrease in relative duplex luminescence outpaces selectivity compared to the decrease observed between Complexes 4 and 5. Similarly, the signal produced by Complex 9 in the presence of single-strands is lower than that of Complex 8, however, and especially when comparing to Complexes 5 and 6, it is readily apparent that the duplex interaction is further compromised as a result of substituting two esters and an acid for molecule which possesses an ester and two acids, respectively. It is also clear that the additional ester am) of Complex 9 compared to the other net neutral complex (Complex 6, FIG. 2) further limits the level of single-stranded oligonucleotide coiling. Lastly, the only complex which has three acids, Complex 10, is unique in that it has a net negative charge profile. Although it is difficult to adequately measure all of the luminescent signals produced by these last three systems (Complexes 8, 9, and 10), the latter of the three is virtually impossible to quantify in either the single-stranded or duplexed oligonucleotide environment when compared to the other two. The enhancement factor of Complex 10 was not quantified, but the luminescence response of the net negative complex further lends support to the understanding of how these complexes interact with single-stranded and duplexed oligonucleotides. This new trend in maximum observed luminescence in the presence of DNA duplexes for these complexes bearing three functional groups follows the trend Complex 7>Complex 8>Complex 9>Complex 10. In this case, the electrostatic repulsion of these complexes becomes too significant a barrier for even duplex intercalation to occur.

Figure 5:
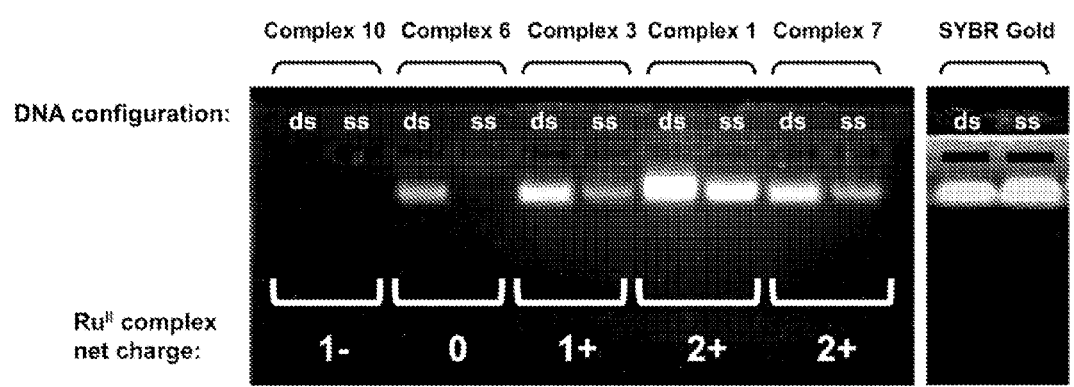
FIG. 5 shows gel electrophoresis results showing the relative intercalative nature of each Ru complex when run in a mixture of ssDNA versus dsDNA samples. Samples included (from left to right) are complex 10, complex 6, complex 3, complex 1, and complex 7. Degree of intercalation is indicated by the relative fluorescence intensities of the individual gel bands. Apparent from the differential staining of the DNA in each lane is that the neutral $Ru^{II}$ complex can distinguish ssDNA from dsDNA, whereas the more positively charged Ru complexes cannot. Electrostatic repulsion between the negatively charged Ru complex and the negatively charged DNA backbone may significantly hinder intercalation, thus resulting in little to no fluorescence even in the presence of dsDNA. The gel to the right shows single and double stranded DNA samples post staining with the commercially available 1×SYBR Gold stain (Invitrogen) for comparison.

In addition to studying the relative luminescence trends for each intercalator by solution based fluorescence spectroscopy, these effects were also investigated in the context of DNA staining in a gel electrophoresis assay. Solutions containing 40 µM of ssDNA or dsDNA were mixed with 25 µM of each complex in water and run in a 1% agarose gel (FIG. 5). The relative selectivity exhibited by each complex for intercalating dsDNA within the agarose gel matched well with the trends observed in solution. Of particular interest is the photoluminescent staining response of the neutral complex 6, which managed to selectively stain only duplexed DNA within the window of fluorescence sensitivity of the gel scanners detectors.

In conclusion, a previously known luminescent DNA intercalator was manipulated to study the hypothesis that the local environment around the complex dictates the extent to which it produces a luminescence response in the presence of hybridized versus unhybridized oligonucleotides. Three complete sets of complexes were generated, each set taking advantage of the modular and sequential addition of ligands toward the synthesis of ruthenium complexes and a ligand whose structure enables the synthetic introduction of either one or two functional groups, so that complexes bearing one, two, or three functional modifications and in varying ratios of esters to acids could be compared. Perhaps the more interesting of these is the set of four complexes that each have three functionalized arms (Complexes 7-10, FIG. 3), a class of complex which recapitulates the structure-activity relationships observed within the other two sets and among all ten complexes studied overall. The increased selectivity follows the same trend, namely, that decreasing steric accessibility while also increasing polarity within the environment around the intercalating moiety leads to better enhancements by limiting unhybridized single-strand interactions and translating to better duplex selectivity. However, although the interactions between complexes and single-strands may be reduced to virtually negligible values, there is a point at which the complexes no longer favorably interact with duplexes and it seems to occur profoundly in the final set of molecules which contain three functional groups per ruthenium complex. The complexes which maintain over two orders of magnitude enhancement in duplex selectivity without significantly altering their ability to luminesce in the presence of DNA duplexes can enable the development of biological assays used to detect hybridization events in oligonucleotide solutions or in the context of gel electrophoresis stains.

Organometallic Complexes

Provided herein are organometallic complexes having a structure M(Het)(Het)(L), wherein M is Ru or Os; each Het is independently bipyridyl or phenanthrolinyl, bipyridyl substituted with one or more of $C_{1-6}$alkyl and $C_{1-10}$alkylene-$CO_2R$, or phenanthrolinyl substituted with one or more of $C_{1-6}$alkyl and $C_{1-10}$alkylene-$CO_2R$, and R is null, H, $C_{1-6}$alkyl, or an oligonucleotide moiety; and L is a structure:

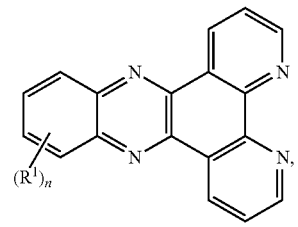

wherein n is 0-3, and each $R^1$ is $C_{1-6}$alkyl, CN, $NO_2$, $OC_{1-6}$alkyl, $CO_2H$, or $CO_2C_{1-6}$alkyl, with the proviso that when n is 0 at least one Het is substituted with $C_{1-10}$alkyl-$CO_2R$. In various cases, n is 0. In various cases, M is Ru.

As used herein, phenanthrolinyl refers to 1,10-phenanthroline.

As used herein, bipyridyl refers to 2,2'-bipyridyl. In some cases, bipyridyl can be substituted with methyl groups, e.g., 2 methyl groups. In some cases, at least one Het is:

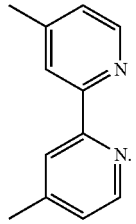

In some cases, at least one of Het (or each Het) is

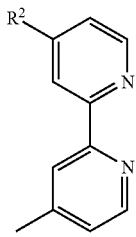

and $R^2$ is $C_{1-10}$alkylene-$CO_2R$. In some cases, at least one Het (or each Het) is

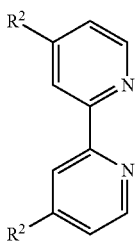

and each $R^2$ is the same and is $C_{1-10}$alkylene-$CO_2R$. In some cases, one Het is

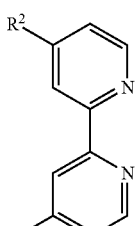

and the other Het is

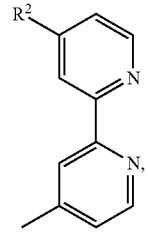

and each $R^2$ is $C_{1-10}$alkylene-$CO_2R$. In various cases, the R of the substituted bipyridyl is null, H, methyl or ethyl. In some cases, the R comprises an oligonucleotide moiety.

Oligonucleotides

An oligonucleotide moiety can be introduced to the carboxy functional group of the $C_{1-10}$alkylene-$CO_2$ on a Het by incorporation, for example, of a 3'-amino modifier group to the oligonucleotide, then subsequent reaction of that amino group with the carboxy functional group to form an amide linkage. Other linkage strategies to append an oligonucleotide to the carboxy of the Het can be employed as readily understood by the synthetic chemist.

The oligonucleotides contemplated can comprise naturally occurring and unnatural nucleotides, alternatively referred to as nucleobases. Naturally occurring nucleobases include adenine (A), guanine (G), cytosine (C), thymine (T) and uracil (U) as well as non-naturally occurring nucleobases such as xanthine, diaminopurine, 8-oxo-N6-methyladenine, 7-deazaxanthine, 7-deazaguanine, N4,N4-ethanocytosin, N',N'-ethano-2,6-diaminopurine, 5-methylcytosine (mC), 5-($C_3$-$C_6$)-alkynyl-cytosine, 5-fluorouracil, 5-bromouracil, pseudoisocytosine, 2-hydroxy-5-methyl-4-tr-iazolopyridin, isocytosine, isoguanine, inosine and the "non-naturally occurring" nucleobases described in Benner et al., U.S. Pat. No. 5,432,272 and Susan M. Freier and Karl-Heinz Altmann, 1997, Nucleic Acids Research, vol. 25: pp 4429-4443. The term "nucleobase" also includes not only the known purine and pyrimidine heterocycles, but also heterocyclic analogues and tautomers thereof. Further naturally and non-naturally occurring nucleobases include those disclosed in U.S. Pat. No. 3,687,808 (Merigan, et al.), in Chapter 15 by Sanghvi, in Antisense Research and Application, Ed. S. T. Crooke and B. Lebleu, CRC Press, 1993, in Englisch et al., 1991, Angewandte Chemie, International Edition, 30: 613-722 (see especially pages 622 and 623, and in the Concise Encyclopedia of Polymer Science and Engineering, J. I. Kroschwitz Ed., John Wiley & Sons, 1990, pages 858-859, Cook, Anti-Cancer Drug Design 1991, 6, 585-607, each of which are hereby incorporated by reference in their entirety). In various aspects, oligonucleotides also include one or more "nucleosidic bases" or "base units" which include compounds such as heterocyclic compounds that can serve like nucleobases, including certain "universal bases" that are not nucleosidic bases in the most classical sense but serve as nucleosidic bases. Universal bases include 3-nitropyrrole, optionally substituted indoles (e.g., 5-nitroindole), and optionally substituted hypoxanthine Other desirable universal bases include, pyrrole, diazole or triazole derivatives, including those universal bases known in the art.

The oligonucleotide contemplated comprises about 5 to about 150, 300, 600, 1200 or more nucleotides in length, about 5 to about 90 nucleotides in length, about 5 to about 80 nucleotides in length, about 5 to about 70 nucleotides in length, about 5 to about 60 nucleotides in length, about 5 to about 50 nucleotides in length about 5 to about 45 nucleotides in length, about 5 to about 40 nucleotides in length, about 5 to about 35 nucleotides in length, about 5 to about 30 nucleotides in length, about 5 to about 25 nucleotides in length, about 5 to about 20 nucleotides in length, about 5 to about 15 nucleotides in length, about 5 to about 10 nucleotides in length, about 400 to about 10,000 nucleotides or more in length, and all oligonucleotides intermediate in length of the sizes specifically disclosed to the extent that the oligonucleotide is able to achieve the desired result. Accordingly, oligonucleotides of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more nucleotides in length are contemplated. When attached to a Het ligand as disclosed herein, the oligonucleotide can be attached using commonly employed linkers for oligonucleotide modification.

As used herein, "hybridization" means an interaction between two or three strands of nucleic acids by hydrogen bonds in accordance with the rules of Watson-Crick DNA complementarity, Hoogstein binding, or other sequence-specific binding known in the art. Hybridization can be performed under different stringency conditions known in the art.

As used herein, "sufficiently complementary" means to hybridize sufficiently well and with sufficient "binding specificity," to: (i) associate with a binding partner and/or (ii) give the desired disruption of the function of a target molecule. Similarly, "sufficient charge" is used herein to describe an amount of charge (i.e., a positive or negative charge) that allows two compounds described herein to associate with one another.

EXAMPLES

Ligands:

The ligands dipyridophenazine[11] and bpy'-$CO_2R$[12] were prepared using established literature protocols. 4-Methyl-4'-butyric acid-2,2'-bipyridyl (dmb'-$CO_2H$), and 4-Methyl-4'-butyric acid methyl ester-2,2'-bipyridyl (dmb'-$CO_2CH_3$) were prepared using established literature protocols.

Ligand bpy"-$(CO_2R)_2$ was prepared using a method analogous to the singly-functionalized bipyridine. Briefly, a 200 mL schlenck bulb flask with 10 cm$^2$ tetrahydrofurane was cooled to −78 degrees Celsius. Approximately 3.3 mL diisopropylamine (23 mmol) followed by 15.2 mL n-butyl-lithium (1.6 M in hexanes; 24 mmol) were added to the cooled reaction flask by syringe. After stirring for approximately 20 min, 2.064 g of 4,4'-dimethyl-2,2'-bipyridine (11.09 mmol) dissolved in 70 cm$^2$ tetrahydrofuran was added via syringe at a drop-wise rate of 3.5 mL/min. At the 2 h mark, the reaction was allowed to warm to room temperature and stir for approximately 14 h under nitrogen. The reaction was rotovapped to dryness and redissolved in 50 cm$^2$ methylene chloride, transferred to a 1 L separatory funnel along with 200 mL brine, and extracted 4×50 cm$^2$ portions methylene chloride. The organic layers were combined, dried over sodium sulfate, and filtered through a 60 mL sintered glass frit. Removal of the methylene chloride under vacuum yielded 4.35 g of a light, amber oil, which was approximately 90% pure by CDCl$_3$ $^1$H NMR and crystallized overnight. Attempts to purify the oil by column chromatography using 550 cm$^2$ deactivated silica (5% triethylamine in hexanes), which is a deviation from the alumina system used in the literature protocol, provided adequate separation but with poor overall yield of recovery. The literature protocols for the subsequent hydrolysis, oxidation, and esterification reactions were all closely followed and provided near-quantitative yields at every stage of the process.

4,4'-bis(butyric acid methyl ester)-2,2'-bipyridyl (dmb"-$\{CO_2CH_3\}_2$)

Synthesis:

Ligand dmb"-$\{CO_2CH_3\}_2$ was prepared using a method analogous to the mono-functionalized bipyridine used above. THF (10 mL) was cooled to −78° C. Diisopropylamine (3.3 mL, 23 mmol) was added via syringe followed by the addition of n-butyllithium (1.6 M in hexanes; 15.2 mL, 24 mmol). After stilling for 20 min, a solution of 4,4'-dimethyl-2,2'-bipyridine (2.064 g, 11.09 mmol) in THF (70 mL) was added via syringe at a rate of 3.5 mL/min After 2 hours stirring at 78° C., the reaction was allowed to warm to room temperature and stirred for 14 hours. The solvent was removed in vacuo and the residue was redissolved in methylene chloride (50 mL), transferred to a 1 L separatory funnel along with brine (200 mL), and extracted with methylene chloride (4×50 mL). The organic layers were combined, dried over sodium sulfate, and filtered through a sintered glass frit. Removal of the methylene chloride under vacuum yielded 4.35 g of a light amber oil that crystallized overnight. The material was approximately 90% pure by $^1$H NMR spectroscopy. Attempts to purify the oil by column chromatography on deactivated silica (5% triethylamine in hexanes) provided adequate separation but with poor recovery. The literature protocols for the subsequent hydrolysis, oxidation, and esterification reactions provided near-quantitative yields.

Ru(dppz)(DMSO)$_2$Cl$_2$ Mono-Ligated Complex:

This method is adapted from reports that also use Ru(DMSO)$_4$Cl$_2$ and one equivalent of diimine ligand in refluxing chloroform or toluene. (see, e.g., Evans et al., J. Chem. Soc. Dalton Trans., 1973(2): 204). Briefly, Ru(DMSO)$_4$Cl$_2$ (234.7 mg, 0.484 mmol, 1.03 equiv.) and dipyridophenazine (129.8 mg, 0.460 mmol, 1.00 equiv.) were refluxed in toluene (15 mL) for 8 hours with vigorous stirring in low light conditions. The reaction was filtered hot in air through a fine sintered glass frit. The fine orange solid, which remained was washed with toluene (2×10 mL), diethyl ether (3×60 mL), and dried in vacuum (244.1 mg, 0.400 mmol, 83% yield). $^1$H NMR (400 MHz, DMF-d$_7$) δ 10.33 (dd, J=5.4, 1.0 Hz, 1H), 10.15 (dd, J=5.3, 1.3 Hz, 1H), 9.80 (dd, J=8.1, 1.2 Hz, 1H), 9.69 (dd, J=8.1, 1.1 Hz, 1H), 8.59-8.46 (m, 2H), 8.38 (dd, J=8.1, 5.4 Hz, 1H), 8.27-8.13 (m, 3H), 3.61 (d, J=12.2 Hz, 6H), 3.12 (s, 3H), 2.45 (s, 3H).

Ru(dppz)(dmb-($CO_2CH_3$)Cl$_2$ Bis-ligated Complexes (n=1,2):

In a typical reaction, the mono-ligated complex (100 mg) and 1.01 equivalents of ester-functionalized ligand (dmb'-$CO_2CH_3$ or dmb"-$\{CO_2CH_3\}_2$) were suspended in refluxing DMF (3 mL) for 4 hours with vigorous stirring in low light conditions. Within minutes, the reagents dissolved and a purple-black solid precipitated. The reaction was cooled to room temperature, diluted with acetone (15 mL), and cooled to −20° C. The suspension was filtered through a fine-porosity sintered glass frit, washed with acetone (2×20 mL) and diethyl ether (3×60 mL), and dried in vacuum. Insoluble, fine microcrystalline products were sufficiently pure for further reactions. (75% yield for Ru(dppz)(dmb'-CO₂CH₃)Cl₂; 59% yield for Ru(dppz)(dmb"-(CO₂CH₃)₂)Cl₂.

Tris-Ligated Complexes:

General Procedures:

Complexes were isolated from their filtered aqueous reaction mixtures by precipitating them with aqueous solutions containing approximately 30 equivalents of sodium hexafluorophosphate and collecting the resulting brightly-colored orange-red solids on a fine-porosity 60 mL fine glass frit. The complexes were subsequently washed 2×5-10 cm² deionized water, 3× full portions diethyl ether, and dried via suction. Characterization of the complexes was typically performed on filtered acetone solutions and the respective chloride salts were re-obtained through precipitation by 10 equivalents of tetrabutylammonium chloride, also dissolved in acetone. These suspensions were centrifuged and washed 2×1 cm² acetone, using 10,500 rpm spin-down conditions at 4 degrees Celsius for 30-40 minutes. The chloride salts were dried under vacuum before redissolving in water for photophysical characterization.

Complex 1:

The parent [Ru(dmb)₂(dppz)] (PF₆) Complex 1 was synthesized using a previously published protocol,[14] which is itself adapted from an earlier report for a similar bis-heteroligated complex.[12] ¹H NMR (400 MHz, Acetone-d₆) δ 9.72 (dd, J=8.2, 1.2 Hz, 2H), 8.71 (d, J=15.3 Hz, 4H), 8.57-8.46 (m, 4H), 8.19 (dd, J=6.6, 3.4 Hz, 2H), 8.07 (dd, J=8.2, 5.4 Hz, 2H), 7.97 (d, J=5.8 Hz, 2H), 7.88 (d, J=5.8 Hz, 2H), 7.51-7.44 (m, 2H), 7.26-7.19 (m, 2H), 2.62 (s, 6H), 2.51 (s, 6H). Mass spectrometry was performed on the chloride salt. ESI-HRMS (We): Calc'd for C₄₂H₃₄N₈Ru [M-2Cl]²⁺ 376.0975; Found 376.0974.

Complex 3, Complex 6, and Complex 10:

Synthesized from their ester counterparts (Complex 2, 4, and 7, respectively, described below) by taking the dried chloride salts and treating with 0.4 M NaOH in 4:1 methanol:water for 10-12 h and by shaking them at 1,000 rpm in 1.5 mL Eppendorf tubes under low light conditions. The reactions were quenched by adding 7 μL glacial acetic acid and the solutions were dried under vacuum. ESI-MS confirms that the saponification reactions proceeded in virtually quantitative yield.

Complex 2, Complex 5, and Complex 9:

Prepared from ~15 mg scale reactions with the Ru(dppz)(bpy'-CO₂CH₃)Cl₂ complex described above. The bis-ligated starting material was massed dry on paper and transferred to a 10 mL schlenck bulb flask along with one equivalent of 4,4'-dimethyl-2,2'-bipyridine (Complex 2), bpy'-CO₂H transferred as an oil (Complex 5), or bpy"-(CO₂H)₂ (Complex 9). Reactions involved refluxing approximately 4 mL 1:1 ethanol:water for 36-48 h with vigorous stilling under the protection of nitrogen and in low light conditions. The work up for these reactions followed general procedures. (87% yield for Complex 2; 77% yield for Complex 5; 72% yield for Complex 9)

Complex 4:

~15 mg scale reaction using one equivalent of the monoligated Ru(dppz)(DMSO)₂Cl₂ complex and two equivalents of bpy'-CO₂CH₃ ligand. The reagents were refluxed in approximately 4 cm² 1:1 ethanol:water in a 10 mL schlenck bulb flask for 36 h under the protection of nitrogen and in low light conditions. The reaction was then allowed to cool to room temperature before diluting with 10 mL deionized water and filtering through a fine-porosity 60 mL sintered glass frit. After collecting the product as a hexafluorophosphate salt, washing, and drying (51% yield), a small amount of complex was redissolved in d-acetone and characterized by ¹H NMR and MS-ESI before exchanging the countercations for chlorides.

Complex 7 and Complex 8:

Prepared from ~15 mg scale reactions with the Ru(dppz)(bpy"-CO₂CH₃)₂Cl₂ complex described above. The bis-ligated starting material was massed dry on paper and transferred to a 10 mL schlenck bulb flask along with one equivalent of bpy'-CO₂CH₃ (Complex 7) or bpy'-CO₂H (Complex 8), both transferred as oils. Reactions involved refluxing approximately 4 mL 1:1 ethanol:water for 36-48 h with vigorous stilling under the protection of nitrogen and in low light conditions. The work up for these reactions followed general procedures. (73% yield for Complex 7; 85% yield for Complex 8)

Oligonucleotides:

Oligonucleotides were synthesized using standard automated phosphoramidite coupling protocols on a BioAutomation MM48 DNA synthesizer and was followed by a well-established deprotection protocol (overnight reaction in 1-2 mL of 28.0-30.0% NH₄OH solution at 55° C. for 17 hours). Oligonucleotides were further purified on a reverse-phase Varian Prostar HPLC using a DynaMax Mocrosorb C18 Column. The optical absorbance of the eluent was monitored at 254/280 nm. All reagents for oligonucleotide synthesis were purchased from Glen Research.

Gel Electrophoresis Assay:

All complexes were dissolved in water along with either single stranded or double stranded DNA, (25 μM intercalator, 40 μM total DNA per lane). 1× loading dye consisting of bromophenol blue and 10% glycerol was added to the samples run in a 1% agarose gel at 90V in 0.5×TAE for 15 minutes. Samples were then visualized using a 365 nm excitation source. For SYBR gold (Invitrogen) staining, the gel was treated with a 1×SYBR Gold solution after the gel was run, followed by imaging.

Absorbance:

Stock solutions of the dried chloride salts were prepared in nano-pure water and diluted accordingly. Measurements were taken on an Agilent Cary 5000 UV-Vis-NIR spectrometer using nano-pure water in the reference positions, scanning from 1000 nm to 200 nm at 600 nm/min. The baseline was corrected for lamp drift by translating the spectra to zero in the 800-900 nm region. The extinction coefficient of the parent complex 1 was taken as 12,400 M⁻¹ cm⁻¹ at 450 nm and the 9 remaining aqueous solutions were matched at 450 nm within 5%.

Fluorescence:

Photoluminescence spectra were collected on a Horiba Jovin-Yvonne Fluorolo®-3 fluorometer at ambient temperature. Concentrations of ruthenium complexes and DNA (3 uM and 10 uM, respectively) were kept constant throughout the experiment (measured with UV-Vis spectrometer). Sample solutions were in 1×PBS. The temperature of the samples was maintained at 20° C. and a thermoelectric cooler was used to maintain the temperature of the solid-state detector at 20° C. The samples were excited with laser at 450 nm using slit sizes of 10×10 nm, collecting fluorescence signals at right angles with respect to the incident light source at 0.5 nm intervals between 540-810 nm with a 0.2 s integration time per interval. All spectra were corrected for the lamp and detector function as well as baselined. The Enhancement Factors (E.F.) were calculated by integrating the signals between 560-800 nm.

REFERENCES

1. Seferos, et al. *J. Am. Chem. Soc.,* 2007, 129(50), 15477-15479.
2. Prigodich, et al., *Anal. Chem.,* 2012, 84(4), 2062-2066.
3. Friedman, et al., *J. Am. Chem. Soc.,* 1990, 112(12), 4960-4962.
4. Hartshorn, et al., *J. Am. Chem. Soc.,* 1992, 114(15), 5919-5925.
5. Song, et al., *Nat Chem,* 2012, 4(8), 615-620.
6. Niyazi, et al., *Nat Chem,* 2012, 4(8), 621-628.
7. Coates, et al., *J. Phys. Chem. B,* 2000, 105(3), 730-735.
8. Jenkins, et al., *J. Am. Chem. Soc.,* 1992, 114(22), 8736-8738.
9. Hudali, et al., *Inorg. Chem.,* 1979, 18(5), 1391-1394.
10. Evans, et al., *J. Chem. Soc., Dalton Transactions,* 1973(2), 204-209.
11. Dickeson, et al., *Aust. J. Chem.,* 1970, 23(5), 1023-1027.
12. Sullivan, et al., *Inorg. Chem.,* 1978, 17(12), 3334-3341.
13. van der Drift, et al., *Eur. J. Inorg. Chem.,* 2002, 2002(8), 2147-2155.
14. Liu, et al., *Inorg. Chem.,* 2001, 40(19), 5045-5050.

What is claimed:

1. An organometallic complex having a structure M(Het)(Het)(L), wherein

M is Ru or Os;

each Het is independently bipyridyl substituted with one or more of $C_{1-6}$alkyl and $C_{1-10}$alkylene-$CO_2R$, or phenanthrolinyl substituted with one or more of $C_{1-6}$alkyl and $C_{1-10}$alkylene-$CO_2R$, and R is null, H, $C_{1-6}$alkyl, or comprises an oligonucleotide moiety; and L is a structure

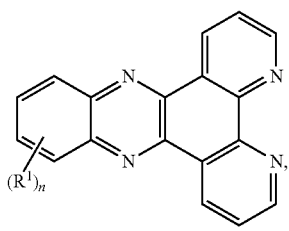

wherein n is 0-3, and each $R^1$ is $C_{1-6}$alkyl, CN, $NO_2$, $OC_{1-6}$alkyl, $CO_2H$, or $CO_2C_{1-6}$alkyl, with the proviso that when n is 0 at least one Het, or each Het, is substituted with at least one $C_{1-10}$alkyl-$CO_2R$, or at least two $C_{1-10}$alkyl-$CO_2R$.

2. The organometallic complex of claim 1, wherein at least one Het is

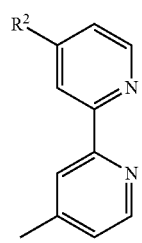

and $R^2$ is $C_{1-10}$alkylene-$CO_2R$.

3. The organometallic complex of claim 2, wherein each Het is

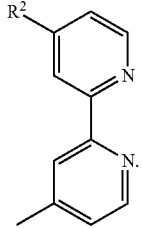

4. The organometallic complex of claim 1, wherein at least one Het is

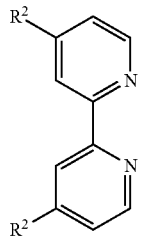

and each $R^2$ is $C_{1-10}$alkylene-$CO_2R$.

5. The organometallic complex of claim 1, wherein one Het is

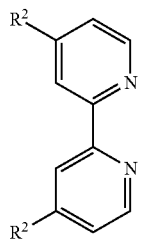

and the other Het is

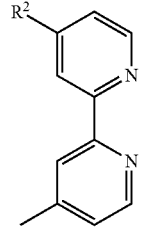

and $R^2$ is $C_{1-10}$alkylene-$CO_2R$.

6. The organometallic complex of claim 1, wherein at least one Het is phenanthrolinyl.

7. The organometallic complex of claim 1, wherein R is null, H, or $C_{1-6}$alkyl.

8. The organometallic complex of claim 1, wherein at least one Het is substituted with a $C_{1-10}$alkylene-$CO_2R$, and R comprises an oligonucleotide moiety.

9. An organometallic complex having a structure selected from Complexes 1, 2, 3, 4, 5, 6, 7, 8, 9, and 10.

10. The organometallic complex of claim 1, being neutral, or having a +1 or +2 charge.

11. The organometallic complex of claim 1, further comprising a chloride or hexafluorophosphate counter anion or a sodium counter cation.

12. A conjugate comprising the organometallic complex of claim 1 and an oligonucleotide, wherein the organometallic complex comprises at least one R comprising an oligonucleotide moiety.

13. A method of determining the presence or concentration of a target molecule in a sample comprising contacting the sample with a complex of claim 1 under conditions that allow association of the target molecule with the complex, wherein upon association of the target molecule and the complex, the complex undergoes a detectable change, said change indicative of the presence of the target molecule.

14. The method of claim 13, wherein the target molecule is double stranded DNA or double stranded RNA, and is selective for double stranded DNA (dsDNA) compared to single stranded DNA (ssDNA) or for double stranded RNA (dsRNA) compared to single stranded RNA (ssRNA).

15. The method of claim 14, wherein the organometallic complex undergoes a detectable change in the presence of dsDNA or dsRNA at least 10 times greater than a detectable change in the presence of ssDNA or ssRNA.

16. The method of claim 13, wherein the detectable change is a change in luminescence.

17. The method of claim 13, for use in gel electrophoresis.

18. The method of claim 13, for use in intracellular detection of the target molecule.

* * * * *